(12) United States Patent
Barritault et al.

(10) Patent No.: US 8,790,631 B2
(45) Date of Patent: *Jul. 29, 2014

(54) USE OF BIOCOMPATIBLE POLYMERS FOR THE PREPARATION OF A COMPOSITION OR A MEDICAL DEVICE

(75) Inventors: Denis Barritault, Paris (FR); Veronique Barbier-Chassefiere, Bouray sur Juine (FR)

(73) Assignees: Organes Tissus Regeneration Reparation Replacement—OTR3, Paris (FR); Denis Barritault, Paris (FR)

( * ) Notice: Subject to any disclaimer, the term of this patent is extended or adjusted under 35 U.S.C. 154(b) by 1779 days.

This patent is subject to a terminal disclaimer.

(21) Appl. No.: 10/577,637

(22) PCT Filed: Oct. 28, 2004

(86) PCT No.: PCT/FR2004/002780
§ 371 (c)(1),
(2), (4) Date: Apr. 28, 2006

(87) PCT Pub. No.: WO2005/041986
PCT Pub. Date: May 12, 2005

(65) Prior Publication Data
US 2007/0141020 A1    Jun. 21, 2007

(30) Foreign Application Priority Data
Oct. 28, 2003 (FR) .................... 03 12605
Apr. 5, 2004 (FR) .................... 04 03550

(51) Int. Cl.
*A61K 31/716* (2006.01)
(52) U.S. Cl.
USPC .................... 424/78.17; 424/488
(58) Field of Classification Search
None
See application file for complete search history.

(56) References Cited

U.S. PATENT DOCUMENTS

| 4,740,594 A | 4/1988 | Mauzac et al. |
| 4,755,379 A | 7/1988 | Jozenfonvicz et al. |

(Continued)

FOREIGN PATENT DOCUMENTS

| EP | 0 093 489 A2 | 11/1983 |
| EP | 1 197 216 A1 | 4/2002 |

(Continued)

OTHER PUBLICATIONS

Vergnolle et al., Trends in Pharmacological Sciences, 22(3), 146-152, 2001.*

(Continued)

*Primary Examiner* — Nissa Westerberg
(74) *Attorney, Agent, or Firm* — Arent Fox LLP

(57) ABSTRACT

The invention relates to a biocompatible polymer having general formula (I) AaXxYy, wherein: A denotes a monomer; X denotes an RCOOR' group; Y denotes an O or N-sulphonate group which is fixed to A and which has either formula —ROSO3R' or —RNSO3R' in which R denotes an optionally branched and/or unsaturated aliphatic hydrocarbon chain which can contain one or more aromatic rings and R' denotes a hydrogen atom or a cation; a denotes the number of monomers; x denotes the rate of substitution of the A monomers by the X groups; and y denotes the rate of substitution of the A monomers by the Y groups. More specifically, the invention relates to the use of said biocompatible polymers for the preparation of a pharmaceutical, dermatological or cosmetic composition or a medical device, which are intended to prevent, relieve and/or treat discomfort, distress, itches, irritations and/or pain and/or to protect tissues against same. In addition, in certain cases, the use of said biocompatible polymers for pain treatment can impact on the actual curing of certain diseases. Significant improvements and even cures have been observed in relation to chronic and painful diseases that are associated with alterations in the extracellular matrix regardless of the origin thereof.

12 Claims, 1 Drawing Sheet

Determination of the general structure of RGTA's

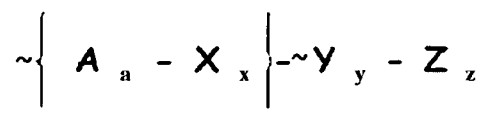

A = monomer
a : number of monomers

X = carboxylic group    Y = sulphonate group    Z = other group
x = substitution rate    y = substitution rate    z = substitution rate

(56) References Cited

U.S. PATENT DOCUMENTS

| | | | |
|---|---|---|---|
| 5,852,003 | A | 12/1998 | Barritault et al. |
| 5,852,004 | A | 12/1998 | Barritault et al. |
| 5,888,984 | A | 3/1999 | Brown |
| 6,342,486 | B1 | 1/2002 | Zulli et al. |
| 6,689,741 | B2 | 2/2004 | Barritault et al. |

FOREIGN PATENT DOCUMENTS

| | | |
|---|---|---|
| FR | 2 461 724 A1 | 2/1981 |
| FR | 2 718 024 A1 | 10/1995 |
| FR | 2 718 025 A1 | 10/1995 |
| FR | 2 781 485 A1 | 1/2000 |
| JP | 8-143460 A | 6/1996 |
| JP | 2002-265369 A | 9/2002 |

OTHER PUBLICATIONS

Bernstein, P. R., Edwards, P. D., & Williams, J. C. (1994). Inhibitors of human leukocyte elastase. Progress in medicinal chemistry, 31, 59-120.*

Escartin et al., *The FASEB Journal*, 17 [6]: 644-651 (Apr. 2003).

Jeanbat-Mimaud et al., *J. Biomater. Sci. Polymer Edn.*, 11 [9]: 979-991 (2000).

English translation of International Preliminary Report on Patentability for International Patent Application No. PCT/FR2004/002780.

Blondin et al., *Mol. Immunol.* 31(4): 247-253 (1994).

Maiga-Revel et al., *Carbohydrate Polymers*, 32: 89-93 (1997).

Barritault et al., "Matrix therapy in vascular pathology: first pilot study to evaluate RGTA Cacipliq 20," presented at the 11$^{th}$ Nationale Conference of wounds and healing, Paris, France (Jan. 14, 2007) and at the 3$^{rd}$ World Union of Wound Healing Societies (WUWHS) Congress, Toronto, Canada (Jun. 4, 2008).

Mangoni et al., "Differential effect triggered by a heparin mimetic of the RGTA family preventing oral mucositis without tumor protection," *Int. J. Radiation Oncology Biol. Phys.*, 74(4): 1242-1250 (2009).

Papy-Garcia et al., "Nondegradative sulfation of polysaccharides. Synthesis and structure characterization of biologically active heparin sulfate mimetics," *Macromolecules*, 38: 4647-4654 (2005).

Ledoux, D. et al., "Human Plasmin Enzymatic Activity Is Inhibited by Chemically Modified Dextrans"; *The Journal of Biological Chemistry*; vol. 275, Issue of Sep. 22; pp. 29383-29390; 2000.

Marc Torrent et al., "The CPC Clip Motif: A Conserved Structural Signature for Heparin-Binding Proteins"; PLoS ONE, vol. 7, Issue 8, e42692, pp. 1-8 (Aug. 2012).

* cited by examiner

Determination of the general structure of RGTA's $$\sim\{A_a - X_x\}-\sim Y_y - Z_z$$

A = monomer a : number of monomers

X = carboxylic group     Y = sulphonate group     Z = other group x = substitution rate     y = substitution rate     z = substitution rate

USE OF BIOCOMPATIBLE POLYMERS FOR THE PREPARATION OF A COMPOSITION OR A MEDICAL DEVICE

CROSS-REFERENCE TO RELATED APPLICATIONS

This application is the U.S. national phase of International Patent Application No. PCT/FR2004/002780, filed on Oct. 28, 2004, which claims priority to French Patent Application No. 0312605, filed Oct. 28, 2003, and French Patent Application No. 0403550, filed Apr. 5, 2004, all of which are hereby incorporated by reference.

The present invention concerns the field of prevention, relief and treatment of pain or discomfort, particularly with regard to comfort, improvement of protection from irritations, tingling or itching. The more specific aim of the invention is the use of biocompatible polymers with a general formula AaXxYy, defined below, for preparation of a pharmaceutical, dermatological or cosmetic composition or a medical device intended for prevention, relief or treatment of discomfort, unpleasant symptoms, irritation and pain of all tissue.

One is acquainted in prior art compounds designated HBG-FPP possessing the ability to accelerate the repair processes of the lesions:
of nervous tissues was described in patient FR 94/03806,
muscular tissues in U.S. Pat. No. 5,852,003, and
of the digestive tract in U.S. Pat. No. 5,852,004.

Also described in patent FR 2781485 was a family of molecules, designated RGTA, which presents remarkable properties, particularly protective effects against free radicals, effects in preventing the formation of fibroses and effects in regulating tissue homeostasis in general and bone tissue homeostasis in particular.

Therefore, RGTA's were described as cicatrisation agents of lesions of the skin, the cornea, flat and long bones, ischaemic tissues such as the tissues of skeletal or cardiac or nervous muscles or indeed irradiated tissues. HBGFPP's and more specifically RGTA's are therefore agents that promote tissular cicatrisation and regeneration in general, regardless of the types of lesions and to the extent that they act as potentialisation and protection agents of the growth factors naturally present in the tissues.

It was also reported in the patient French patent application published under No. 2 718 025 that HBGFPP's are agents presenting anti-inflammatory activities by inhibiting certain inflammation enzymes, such as leukocytic elastase.

Furthermore, the French patient application published under No. 2 461 724 in addition to the U.S. Pat. No. 4,740,594 describe the dextran derivatives containing carboxymethyl, carboxymethyl benzylamide sulphonate residues (carboxylated and sulphated derivatives of dextran) presenting anti-inflammatory activities by inhibition of the complement. More, these same properties were reported for sulphated derivatives of fucanes or dextran devoid of a benzylamine group (Fisher, et al., *Mol Immunol.*, 1994, 31 (4) p 247 and Maiga et al., *Carbohydrate Polymers*, 1997, 32, 89-93).

Independently of the regeneration activities, an activity of biocompatible polymers against pain and pruritus (or itching) has now been demonstrated. Indeed, these compounds show an unsuspected ability to reduce, relieve or suppress pain and pruritus. These effects were observed within a few minutes following application of biocompatible polymers and their action of relieving pain and if appropriate, itching followed by the effect of a feeling of comfort that results lasted several hours or even a few days. These effects are obtained on each new application of biocompatible polymers. These compounds riot only act on injured or irritated tissues, but also on healthy tissues without the tissular lesions necessarily being visible.

These effects of relief on treatment of pain and/or itching in addition to the feeling of comfort were observed in all types of pain and itching, regardless of the origin or the pain or the nature of the tissues involved by location or systemic application or by administration via the oral or aerial route. These effects were more particularly observed in surface tissues in direct contact with the exterior, such as the skin, the cornea or the eardrum or on tissues in indirect contact such as the mucosa of the digestive tract and of the nasal and pulmonary respiratory tracts. Pains in tissues which are deeper and therefore of more difficult access such as muscles, tendons or joints (knees, elbows) or the bones of the foot following orthopaedic surgery were relieved by local application to the skin on the painful area by local or systemic injection in addition to oral administration. Strangely, isolated oral administration also allowed relief of headaches and daily oral administration over several weeks of treatment of chronic painful conditions of the locomotor system or dorsal chronic painful conditions, chronic painful conditions of the nerve tissues, of the mucosa of the digestive or pulmonary tracts and of the skin tissues. Biocompatible polymers may be applied preventively, immediately after the lesion, to the site of the lesion and prevent or significantly diminish the pain. Likewise, application to skin that is uninjured and apparently healthy, but sensitive and giving rise to a sensation of discomfort described in the expression "touchy nerves" results in certain cases in a sensation of comfort and wellbeing; this is likewise the case in elderly persons presenting with dry and rough skin described as "lizard skin". Absorption via the oral route also yields this sensation of comfort and wellbeing. Administration via the aerial route also makes it possible to calm irritation and relieve effects of suffocation, respiratory oppression and cough.

The same applies to the effects of the polymers of the invention in order to calm or relieve pruritus, whether local or generalised. Local application to insect bites, on skins with eczema, psoriasis or simply a non-visible dermatosis or furthermore to the anal or genital mucosa or also to the scalp (to mention only the most striking examples) calms local itching. The same applies to generalised itching which is calmed following oral administrations.

These effects are therefore very different from the effects of stimulation of tissular cicatrisation and regeneration described in prior art, both by their nature and the rapidity with which they are perceived.

Consequently, the aim of the invention is to use a biocompatible polymer corresponding to the following general formula (I):

in which:
A represents a monomer,
X represents a RCOOR' group,
Y represents an O or N-sulphonate group bound to A and corresponding to one of the following formulas

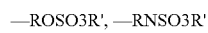

in which:
R represents an aliphatic hydrocarbon chain, possibly branched and/or unsaturated and which may contain one or more aromatic rings and
R' represents one hydrogen atom or one cation.
a represents the number of monomers, x represents the rate of substitution of the A monomers by the X groups, y represents the rate of substitution of the A monomers by Y groups, for preparation of a pharmaceutical, dermatological or cosmetic composition or a medical device intended for the prevention, relief and/or treatment of discomfort, unpleasant symptoms, irritation and/or pain and/or protection of the tissues against the latter.

The A monomers, identical or different, are selected from among the sugars, esters, alcohols, amino acids and nucleotides in order to form a polymeric skeleton of the polyester or polyalcohol or polysaccharide type, or furthermore of the nucleic acid or protein type.

Among the polyesters, they may be biosynthetic or chemically synthesised copolymers such as aliphatic polyesters or those of natural origin such as polyhydroxyalcanoates.

The polysaccharides and their derivatives may be of single-chain bacterial origin, such as the polyglucoses (dextran, cellulose, beta glucan) or originate from other monomers with more complex units such as for the xanthanes (glucose, mannose or glucuronic acid) or furthermore the glucuronans and glucoglucuronans.

The polysaccharides may be of single-chain plant origin, such as cellulose (glucose), or the pectins (galacturonic acid), the fucanes and starch or may be more complex, such as the alginates (galuronic and mannuronic acid), of fungal origin such as steroglucan or of animal origin such as chitins or chitosan (glucosamine).

The present invention concerns, very specifically, polymers with little degradation by the glycanases of mammals and/or bacteria and presenting weak anticoagulant activity. "Little degradation by the glycananases" implies, within the context of the present invention, polymers which, placed in solution with these glycanases, are less than 50% degraded whereas under the same conditions, the glycosaminoglycan substrates of mammals are 100% degraded. A measurement method is given in example 1. "Weak anticoagulant activity" implies, within the context of the present invention, anticoagulant activity less than one tenth of that of heparin (<20 IU). Consequently, the glycosaminoglycans or animal origin such as heparin and heparan sulphates, chondroitins, dermatans or keratin sulphates and hyaluronic acid are excluded from the present invention.

Preferably, the number of A monomers defined in the formula (I) by "a" is such that the mass of the said polymers of formula (I) is greater than approximately 2000 daltons (which corresponds to 10 glucose monomers). Furthermore, the mass of the said polymers of formula (I) is less than approximately 2000000 daltons (which corresponds to 10000 glucose monomers). Favourably, the mass of the said polymers of formula (I) is between approximately 30 and approximately 100 kdaltons.

Preferably, the rate of substitution of all the A monomers by the X groups defined in the general formula (I) by "x" is between approximately 20 and 150% and is preferably on the order of 50%.

Favourably, the rate of substitution of all the A monomers by the Y groups defined in the general formula (I) by "y" is between approximately 30 and 150% and is preferably on the order of 100%.

In the definition of the rates of substitution above, a rate of substitution x of 100% implies that each A monomer of the polymer of the invention statistically contains an X group. Likewise, a rate of substitution y of 100% implies that each monomer of the polymer of the invention statistically contains one Y group. Rates of substitution greater than 100% indicate the fact that each monomer statistically bears more than one group of the type involved; conversely, rates of substitution of less than 100% indicate the fact that each monomer statistically bears less than one group of the type involved.

According to a preferred form for implementing the invention, the R radical in the polymers described above is not benzylamine or benzylamine sulphonate. Indeed, the presence of benzylamine, even though it does not adversely effect the analgesic action, is not desirable, since it is liable to induce a toxicity of the biocompatible polymers of formula (I).

Favourably, the preferred R radicals are selected from a linear or branched alkyl, allyl or aryl group.

The biocompatible polymers used in the context of the invention may also comprise functional groups Z, different from X and Y and capable of bestowing additional biological or physical and chemical properties on the said polymers. The general formula of the biocompatible polymers containing in addition a Z group usable within the context of the present invention is given in FIG. 1 in the appendix.

Preferably, the rate of substitution of all the A monomers by Z groups represented by "z" in FIG. 1 is between 0 and 50% and preferably on the order of 30%.

Favourably, the Z group in the biocompatible polymers usable within the context of the present invention is a substance capable of bestowing on the said polymers improved solubility or lipophilia or furthermore of reducing the anticoagulant activity.

In an initial form of implementation, the Z groups in the biocompatible polymers usable within the context of the present invention are identical or different and are amino acids, fatty acids, fatty alcohols, ceramides or derivatives thereof, or furthermore addressing nucleotide sequences.

In a second form of implementation, the Z groups in the biocompatible polymers usable within the context of the present invention are identical or different and are therapeutic agents.

The X, Y and Z groups may be bound directly to the A monomer or bound to each other, one only being bound to the A monomer.

Therefore, the Z groups may be bound by covalence directly to the A monomers or bound by covalence to the X and/or Y groups.

However, the Z groups may also be conjugated to the polymers of formula (I) by other than covalent bonds, such as ionic or hydrophilic interactions, according to the nature of A, X and Y.

During her work, the Applicant tested biocompatible polymers based on glucose, such as those derived from dextran, cellulose or beta glycan or based on glucuronan or glucoglucuronan or fucanes or furthermore alginates. These polysaccharides were transformed into RGTA by addition of carboxylic and sulphate groups and Z substitutions of different types and the structures are summarised in table 1 below.

Also tested were polyester biocompatible polymers such as the copolymer of malic acid described in the publication of Jeanbat-Mimaud et al. ("Bioactive functionalized polymers of malic acid for bone repair and muscle regeneration", *Journal of Biomaterial Sciences*, Polymer Edition, 2001, vol. 11, p979-991)

Therefore, the Applicant's work has made it possible to show that local application of biocompatible polymers during treatment of skin lesions originating, for example, for superficial burns, such as exposure to the sun or laser radiation (resurfacing) or deep burns, or furthermore ulceration due to vascular or diabetic disorders causing major suffering, made it possible to relieve the patients of this suffering within the initial hours following tissue aggression and therefore well before the cicatrisation process is observable. In extreme cases in which these patients had been under powerful analgesics such as morphine for example, the effect of relief was rapidly perceptible following application of the biocompatible polymers and the analgesic effect was so powerful that after about a fortnight, these patients no longer needed any analgesic treatment, whereas in some of the examples, these patients had been under morphine for two years. Also unexpectedly, the same types of skin pain were relieved after oral administration of the biocompatible polymers of the invention.

Still in the acase of skin lesions, the Applicant observed a reduction in the suffering related to chapping or furthermore cold sores, with their limbial ulceration induced being both less painful and more limited.

A striking effect in terms of relief of pain and pruritus was observed against painful scars. An accompanying effect of this relief after several weeks of repeated applications of biocompatible polymer is, in addition to a major reduction in pain, an aesthetic improvement in the scar with a finer, less visible mark and redness that has reduced or disappeared.

Likewise, the painful effects induced by insect bites were reduced. Generally speaking, the Applicant observed the effects against pain by simple application of biocompatible polymers to all the skin lesions and irritations, including those of the scalp. The lesions could be of all origins, in addition to those in serious diseases such as psoriasis or other disorders adopting hyperkeratotic forms, in contact dermatitis or during mechanical irritation or that caused by chemical products. This soothing effect of the biocompatible polymer of the invention on pruritus and pain was observed in many cases following oral administration or local application, whether the pruritus and/or pain was generalised, occasionally diffuse, such as that caused by eczema, mycoses, parasites, viruses such as in herpes zoster, or chickenpox, drugs, hormonal disorders (such as diabetes, hyperthyroidism), or chronic renal insufficiency or haematological disorders such as Hodgkin's disease or polyglobulia, other furthermore whether the pruritus or pain was local, regardless of the origin.

The same observations were obtained for suffering in tissues other than the skin and in particular those in direct contact with the environment. Therefore, during treatment of corneal ulcers, we observed relief in the animals and much better treatment acceptance, as if this treatment relieved the pain due to the ulceration and indeed from the initial minutes onwards following ulceration. The effects of relief observed according to the cases lasted several hours and were repeated at each of the instillations of the biocompatible polymers.

The Applicant observed that acid stomach pains are very rapidly relieved by administration of biocompatible polymers. The same applies to cases of lesions of the gums and the tissues of the mouth which, on the whole, are rapidly relieved following a mouthwash and brushing the teeth with a solution of biocompatible polymers. These effects were also observed in case of toothache. Aphthous ulcers do not give rise to this burning sensation and seem less sensitivity to aggressions such as exposure to acid or caustic foods. Likewise, irritation and pruritus of the anal or genital mucosae is relieved by application of biocompatible polymers as a solution or a cream.

This same relief was observed after pulmonary intoxications and burns originating from inhalation of smoke derived from fires or toxic gases. In this case, the biocompatible polymer was inhaled after being prepared as an aerosol. In the case of persons suffering from asthma, chronic or acute bronchitis and obstruction of the airways, inhalation of the biocompatible polymers of the invention in the form of an aerosol induced a calming effect allowing relief of pain and a reduction in respiratory oppression. It also resulted in a reduction in the bouts of coughing and relief of throat pain. The effects are particularly marked for individuals sensitive to cigarette smoke, which may result in irritation of the throat and coughing bouts, both in smokers and those around them. An effect and relief were also observed after inhalation of the biocompatible polymers of the invention in the case of persons suffering from rhinitis, the nasal mucosae of whom are rapidly irritated and become a source of discomfort, pruritus and sometimes suffering. These effects against pain, against pruritus and of comfort were observed very rapidly after inhalation as nasal aerosol or spray and a further exposure to the biocompatible polymers was administered as soon as the pains returned. Interestingly, these inhalations became less and less frequently necessary, with pain returning at greater intervals. Very surprisingly, as the effect of relief of pain and discomfort was observed with the treatment with the polymers of the invention, disorders such as asthma, allergic or non-allergic rhinitis and even chronic bronchitis resolved, since after several months and discontinuation of administration of the polymer, none of the symptoms of these diseases returned.

Likewise, the Applicant observed that local injection or application as an ointment of the biocompatible polymers on the painful areas of the tendons, such as for the elbow, the hand or furthermore the knee, rapidly and durably relieves the pain. Therefore, against several types of tendonitis of the elbow such as "tennis elbow", or painful tendonitis of the hand preventing grasping of an object or ischaemic tendonitis of the knee, such as in Osgood-Schlatter's disease or furthermore against pains in the tendons of the feet such as the Achilles tendon in athletes, effects in relieving pain were observed. The same treatment was applied to racehorses suffering from tendonitis of the joint areas of the legs. Therefore, a series of injections of a few microliters of biocompatible polymers at 100 micrograms per milliliter in the peritendinous area allowed relief of pain and this relief was indicated by an absence of claudication after approximately a fortnight. The treatment was continued with a frequency of one week and resumption of training after two months showed absence of pain on palpation. In several of these examples, the painful area showed hypertrophy on being touched. An interesting effect of the treatment was the reduction and suppression of this area as the pain diminished. Likewise, in the case of Duputyren's disease, relief of the pain in the joints of the phalanges and the metacarpals was observed and to our surprise, application in the long term also improved functioning of the joint and allowed a significant recovery of movement of the fingers with a visible reduction in the thickening and the retraction of the palmar aponeurosis. Therefore, the polymers of the invention not only have effects on pain, but improve the functional status of the locomotor system, particularly in chronic destructive diseases of the matricial tissue, such as those observed in the different forms of arthritis, tendonitis and of the vertebral column.

Observations of relief were also reported after local administration of biocompatible polymers in cartilage lesions, either by intra-articular injection of biocompatible polymers alone or in combination with hyaluronic acid or after percutaneous administration by massages around the joint. These same effects of relief and sometimes suppression of pain were obtained by repeated absorptions by the oral route of the solution of biocompatible polymers of the invention in persons suffering for a long period from joint pains of the knees, of the hip and/or of the back. This same effect of pain relief was observed in persons suffering from joint pains and spasms of the limbs or viscera in addition to spasms in neurodegenerative diseases or neuromuscular disorders as varied as multiple sclerosis or Parkinson's disease. Surprisingly, daily repeated oral administration of the polymer of the invention over several weeks not only reduced the pain but the partial recovery of motricity was observed in the case of multiple sclerosis on an almost paralysed leg in addition to almost normal recovery of digestive transit. This functional recovery of motricity shows that the polymers of the invention, in addition to their properties against pain, may improve treatment of chronic destructive diseases of matricial tissue such as those of the nerve sheaths.

The effect of the polymers of the invention on digestive tract pain was also observed in the case of Crohn's diseases or chronic proctocolitis. Several patients suffering from these diseases, subject to diffuse abdominal pains, took biocompatible polymers via the oral route prepared as a solution in water, the objects of the invention, with very marked effects on the pain experienced in the abdomen. After one to two months of twice daily administration of 50 milliliters of a solution ranging from 1 microgram to 1 milligram per ml of solution, these persons observed an improvement in their suffering accompanied by better transit and normal stools. Therefore, surprisingly, the treatment of pain by the polymers of the invention also improved the state of health of the patients over a period of several months without any signs of recurrence. Therefore treatment of chronic diseases of the digestive tract causing sustained destruction of the digestive tissular matrices using the polymers of the invention relieves the pain and significantly improves the condition of these patients.

Analgesic effects were also observed following orthopaedic joint surgery. Therefore, surgery aiming to straighten the metatarsal bones in patients suffering from hallux valgus and deformation of the other toes is very painful and the patient suffers on awakening and for several days. Injection of biocompatible polymers via the intramuscular route on the day after the operation and after a night of major pain in spite of administration of powerful analgesics brought about marked relief which persisted for 1 day. Repeated injection on the $4^{th}$ and $8^{th}$ day allowed the patient pain-free convalescence whereas without this treatment based on biocompatible polymers, the pain persists for several weeks and the patient only obtains relief by concomitant analgesic treatment. The same is reported to apply for other types of surgery.

Consequently, the present invention concerns the use of a biocompatible polymer such as that described above for preparation of a pharmaceutical or dermatological composition or a medical device intended to prevent, relieve and/or treat pains induced by lesions or irritations or pruritus in an individual in an area in contact with an outside medium.

Within the context of the present invention, "lesions or irritations of an area in contact with an outside medium" implies both skin lesions or irritations, lesions or irritations or stinging of the cornea, lesions of the eardrum, lesions or irritations and/or pruritus of the digestive tract (mouth lesions, anal lesions and pruritus, stomachal lesions, etc. . . . ), lesions or irritations of the respiratory tract such as lesions of the tissues of the airways and the lungs and lesions or pruritus of the urogenital tract. Preferably, the pains of the lesions, either open or cicatrised, the skin irritations and/or pruritus which the compositions or medical devices containing biocompatible polymers as described in the invention are intended to prevent, relieve and/or treat are selected from among lesions induced by superficial burns due to exposure to the sun or laser radiation, irritations and pruritus of the nose or the throat causing coughing bouts, ulceration due to vascular or diabetic disorders, chapping, limbial ulcerations caused by cold sores, lesions or pruritus caused by insect bites, by mechanical irritation or by chemical products such as acids, hyperkeratotic diseases such as psoriasis or contact eczema and dermatitis.

The present invention also concerns the use of a biocompatible polymer such as that described above for the preparation of a pharmaceutical composition or a medical device intended to prevent, relieve and/or treat pains in the tendons, cartilages, joints and/or of the back and in general pains associated with the locomotor system.

"Pain in the tendons" implies, in the context of the present invention, both pains caused by tendonitis in the tendons of the foot, hand, elbow or in the joints and pains caused in ischaemic tendons such as in Osgood-Schlatter's disease or pains caused following rupture of the ligaments (Achilles tendon, cruciate ligaments of the knee, etc. . . . ).

"Pain in the cartilages or joints" implies, within the context of the present invention, both pains caused by injured cartilages in the joints such as the knees, the hip and in the back (lumbar and cervical vertebrae and intervertebral discs), with the effects of pains transmitted by the nerves being also perceived at a distance in the neck, the arms or the legs.

Pain in the locomotor system implies, within the context of the present invention, the pains in the tendons and joints identified above, but also diffuse or localised pains in general such as those of neuromotor disorders such as multiple sclerosis, Parkinson's disease, Lou Gehrig's disease, chorea, motor ataxia in general or those types resulting from nerve compression or furthermore diabetic neuropathies.

The present invention also concerns the use of a biocompatible polymer such as that described above for preparation of a pharmaceutical composition or a medical device intended to prevent, relieve and/or treat pains in the muscles and in general, following an impact and/or diffuse pains such as diffuse pains in the abdomen and the head such as headaches.

Therefore, following an impact received while practising a sport such as rugby or football (on the legs, for example), local application of the biocompatible polymer allowed very rapid elimination or reduction of the pain, in addition to resumption of the activity by the athlete.

More generally, diffuse pains in many cancers may benefit from treatment via the oral route with biocompatible polymers with the aim of relieving pain, without however claiming any therapeutic action. Effects of relief were observed, as in the case of cancers of the pancreas, the liver, the kidneys or in bone or lung metastases. Treatment with biocompatible polymers allowed a reduction in the doses of morphine required in order to calm the pains of these patients.

The aim of the present invention is therefore to offer a new method of preventing, relieving and/or treating the pains listed above and/or of protecting the tissues against the latter. These methods consist in administering a pharmaceutically effective quantity of a pharmaceutical composition containing a biocompatible polymer such as that described above or in using in an appropriate manner a medical device based on a biocompatible polymer such as that described above.

Surprisingly, the effect of treatment of pain by the biocompatible polymer also resulted in certain cases in a significant improvement or even an apparently complete cure of the disease or the lesion which is itself the cause of the pain. This was observed in many cases that were never described.

Therefore treatment of the pain and pruritus of recently closed but also old scars allowed in addition a significant improvement in the quality of the scar with a reduction in hypertrophy, width and redness of the scar.

Therefore, treatment of the respiratory discomforts and pains resulted in an improvement in the disease itself that caused the pain. This improvement was notable in the case of treatment of cystic fibrosis and in certain cases such as in asthma, rhinitis and pulmonary emphysema. An apparent cure was observed for at least a few months.

Therefore in the case of treatment of pains in the locomotor system, the pain relief observed as the treatment progressed resulted in significant increase in motricity, as in the case of multiple sclerosis, rheumatoid arthritis, arthrosis, back pains and sometimes total functional recovery, as in many cases of tendonitis. A more surprising fact was the relief of pain in the case of multiple sclerosis and in these patients suffering from paralysis of a limb, slight but significant motor recovery after several weeks of oral administration of an aqueous solution at 100 micrograms per ml of the polymer of the invention.

The polymers of the present invention are not intended to treat the cause of the various different lesions causing the pain or the itching, but act in a general manner on the painful tissue within short periods following administration. This rapidity of action does not at first sight correspond to an action against the causes themselves. We do not observe the disappearance of the disease such as diabetes even by relieving the associated neuropathy.

In general, diseases of all origins that cause local destruction of the extracellular matrix at the tissue sites affected, regardless of whether these diseases are chronic or not, of infectious, viral or bacterial origin and of autoimmune, metabolic, ischaemic or degenerative origin, all have in common the effect of inducing a local reaction through enzyme activations which in particular destroy the glycosaminoglycans of the matrix.

The biocompatible polymer is combined in the drugs (i.e. pharmaceutical composition or medical device) according to the invention with any pharmaceutically acceptable vehicle known to the one skilled in the art adapted to the mode of administration used. Therefore, the drugs according to the invention may be administered via the systemic, local or oral route, or as an implant in the form of an ointment, a cream, a mouthwash, an aerosol or an injection, etc. The examples that follow describe more precisely preferred modes of administration of the compositions used within the context of the present invention.

The present invention also involves the use of a biocompatible polymer as defined above for preparation of a comfort and particularly cosmetic composition for the prevention and relief of the skin discomfort and unpleasant symptoms such as tingling, irritations, itching and tugging of the skin in addition to protection of the tissues such as the skin, the cornea and the mucosae.

Other advantages and characteristics of the invention will appear from the examples that follow and which concern the preparation and formulation of the biocompatible polymers used within the context of the present invention and which also describe their activity against pain. These examples are given as illustrations only and cannot be interpreted as limiting the present invention.

EXAMPLE I

Preparation, Measurement of Resistance to Glycanases and Formulation of the Biocompatible Polymers 1) Example of Preparation.

The drug is obtained by synthesis from a dextran (Amersham Pharmacia T40 USP). The method of synthesis comprises two stages of chemical grafting, carboxymethylation and O-sulphonation.

a) Carboxymethylation Protocol 75 mL of a solution of dextran T40 (15 g, 92.5 mmol) in Milli-Q water and 48 mL of a solution containing 29.6 g (740 mmol) of caustic soda are prepared simultaneous. The temperature of the two solutions is reduced to 4 C before gently pouring the caustic soda solution into the dextran solution. The reactional mixture is shaken for twenty minutes at 4 C. After gradual addition of 30.6 g (323.8 mmol) of chloroacetic acid, the temperature of the reactional mixture is raised to 50 C for fifty minutes before being neutralised with acetic acid (pH 7).

The solution obtained after cooling is filtered over a 0.45 µm membrane (Millipore), the volume is raised to two liters and sodium chloride is added in order to obtain a final concentration of 1M. The sodium salt of the carboxymethyldextran is purified by ultrafiltration with tangential flow over a membrane with a cutoff threshold of 10 000 daltons (Pellicon®, Millipore). Two successive washings are performed at constant volume, initially with 2.5 L of 1M sodium chloride, followed by 18 L of Milli-Q water. The carboxymethyldextran is concentrated and ultrafiltration system is rinsed with 250 ml of Milli-Q water.

The final solution is dehydrated by lyophilisation.

b) Sulphatation Protocol.

Since CarboxyMethylDextran (CMD), in the form of sodium salt, is insoluble in an organic medium, it is necessary initially to acidify the polymer by percolation over an ion exchange resin (Amberlite IR 120) in order to generate CMDH*. The product is subsequently presented in the form of fluffy white-coloured fibres.

The CMDH*(6 g, 32 mmol) is placed in solution in a mixture of FA (either fatty acid or fatty alcohol) (45 mL), dimethylformamide (DMF) (180 mL) and 2-methyl-2-butene (45 mL) at 30° C. The sulphur trioxide complex, $SO_3$/DMF (24.3 g, 160 mmol) is added to this solution. It is left to react for two hours at 30° C. while stirring. The rectional mixture is neutralized with sodium hydrogenocarbonate ($NaHCO_3$, 5%) to a pH=7.

After filtration over a 0.45 µm membrane (Millipore), the volume is raised to two liters and sodium chloride is added in order to obtain a final concentration of 1M. The sodium salt of the carboxymethyldextran sulphate is purified by ultrafiltration with tangential flow over a membrane with a cutoff threshold of 10 000 daltons (Pellicon®, Millipore). Two successive washings are performed at constant volume, initially with 5 L of 1M sodium chloride followed by 18 L of Milli-Q water. The carboxymethyldextran sulphate is concentrated and the ultrafiltration system is subsequently rinsed with 250 ml of Milli-Q water.

The final solution is dehydrated by lyophilisation. The degree of substitution (ds) of the carboxymethyl groups (dsCM) is defined as being the degree of substitution per unit of glucose of the carboxymethyl groups and the ddD is defined as the degree of substitution per unit of glucose of the sulphate groups. The product OTD 70 obtained fulfils the following analytical criteria:

dsCM: 0.25 to 0.75
dsS: 0.80 to 1.30

In the above examples, the biocompatible polymers were prepared in a solution of physiological saline.

2) Measurement of Resistance to Digestion by Glycanases.

A comparative study of the effects of the glycanases on the RGTA's and on the natural substrates which the glycosaminoglycans of mammals are. The glycanases used are obtained from Sigma (US) and are the chondroitinases ABC, heparitinase 1 and heparinase. The hyaluronidase is from Seikagaku (Japan). All these enzymes are of bacterial origin.

The first two are placed in solution by 2 units in 100 µl of 100 mM acetate buffer at pH 7.4, whereas the heparitinases and heparinases are at 50 milliunits per ml of 10 mM sodium acetate buffer pH 7.0, with 0.5 mM of calcium acetate and 100 µg/ml of BSA.

The GAG reference substrates were chondroitin sulphate A (CSA) of bovine origin, chondroitin B (CSB) of porcine origin, chondroitin sulphate C(CSC) from shark cartilage and heparin (HS) of bovine origin. These GAG were placed in solution at 200 mg/ml in acetate buffer at 100 mM at pH 7.4. The RGTA's were placed in solution at 400 mg/ml.

The incubation conditions were 6 hours at 37° C. and formation of fragments after digestion by these enzymes was performed after marking of the GAG of the reactional medium with anthracic acid (Fluka); preparation by HPLC is performed using an exclusion column TSK 3000 PWXKL no. 3 PWXO4B333_in a mobile phase of phosphate buffer in 1M NaCl under a flow rate of 1 ml/min and an elution time of 120 min. Detection is performed using an infrared detector adjusted to an ion excitation length at 310 nm and emission at 410 nm; the analysis is performed through Eurochrom software. The measurements of the degradation activities of the various different enzymes are calculated by integration of the separate peaks by chromatography according to the reaction time. The area of the peak of the GAG or RGTA at time zero being the frame of reference of 0% degradation.

TABLE 1

| | Glycanase | | | |
|---|---|---|---|---|
| | ChA BC | Hyaluronidase | Heparinase | Heparitinase |
| CSA | 100 | | 7.2 | 26.2 |
| CSB | 100 | | 12 | 27 |
| CSC | 100 | | 20 | 25 |
| Heparin | 100 | | 100 | 100 |
| Hyaluronic Acid | | 100 | 100 | 100 |
| RGTAOTD120 | 20 | 25 | 23 | 23 |
| RGTAOTD70 | 20 | 22 | 27 | 15 |
| RGTA-E87 | 10 | 10 | 15 | 15 |

TABLE 1-continued

| | Glycanase | | | |
|---|---|---|---|---|
| | ChA BC | Hyaluronidase | Heparinase | Heparitinase |
| RGTA-G-36 | 5 | 5 | 5 | 5 |
| RGTA-E82 | 5 | 5 | 5 | 5 |
| RGTA-21 | 5 | 5 | 5 | 5 |
| RGTA-E61 | 5 | 5 | 5 | 5 |
| RGTA-E57 | ND | ND | 5 | ND |
| RGTA-MP4 | ND | ND | 5 | ND |
| RGTA-FU | ND | ND | 5 | ND |
| RGTA-LG | ND | ND | 5 | ND |
| RCTA-XA | ND | ND | 5S | ND |

6) Formulations.

The preparations used by local administration are at concentrations of 100 micrograms of biocompatible polymers per milliliter of solution or ointment (final volume) unless indicated otherwise. The modes of local application involved direct depositing of drops on the painful lesion, instillation, absorption via the oral route, contact by rinsing the mouth, ingestion, by aerosol, inhalation, by impregnation of a gauze or a dressing and application of the gauze or impregnated dressing to the painful area, by subcutaneous injection in the vicinity of the painful area.

As an ointment formulation, the following compositions were prepared using sodium carboxymethylcellulose gel (Aqualon) at 4.5% complement at 100% or furthermore a neutral hydroxypropylcellulose gel (Kucel of Aqualon type 99MF EP) at 3% complement at 100% or furthermore hydricerine at 33% (O/W (hydrophilic phase dispersed in a lipophilic phase, such as the excipient from Roc® containing Vaseline, liquid paraffin, glycerides, polyoxylene ethers and cerisine) complement at 100%.

A particularly effective formulation for local applications to closed skins consists in using water-free antibacterial gels marketed for washing the hands "antibacterial gels without rinsing". Several of these products based on polyethylene glycol, alcohol and glycerine are easy to obtain (for example, Assanis® from Blue skin®) in which the biopolymer is stable and set at a final concentration of between 0.1 and 1000 micrograms per ml, with a preferred concentration of 100 micrograms).

For injectable solutions via the systemic route, the RGTA was in a solution of physiological saline at 1.5 mg/kg, unless otherwise specified.

Table 2 below specifies the types of biocompatible polymers (molecular weights, types and degrees of substitution) used in the different examples.

TABLE 2

| | Biocompatible polymers | Initial structure | Structure | | | | |
|---|---|---|---|---|---|---|---|
| | | | | | | Substitution degree | |
| Example* | Biocompatible polymers | Initial structure | Mol. weight$^b$ | Z | X = CM x | Y = SO3 y | Z z |
| 1, 3 | RGTAOTD2 01 | Dextran | 2 | — | 0.4-0.5 | 0.7-1 | — |
| | RGTAOTD2 02 | Dextran | 10 | — | 0.4-0.5 | 0.7-1 | — |
| All examples | RGT A OTD70 | Dextran | 40 | — | 0.4-0.5 | 0.7-1 | — |
| 3 | RGTAE-87 | Dextran | 70 | — | 0.39 | 1.10 | — |
| 3 | RGTAC-17 | Dextran | 200 | — | 0.48 | 1.15 | — |
| 3 | RGTAC-6 | Dextran | 500 | — | 0.43 | 1.30 | — |
| 3 | RGTAC-21 | Dextran | 2000 | — | 0.52 | 0.93 | — |
| 1, 3, 5, 6, 7, 8 | RGTAE-97 | Dextran | 40 to 2000 | — | 0.38 | 1.17 | — |
| 1, 3, 5, 8, 10 | RGTAG-36 | Dextran | 10 | Phenylalanine methyl ester | 0.59 | 0.83 | 0.22 |

TABLE 2-continued

| Example[a] | Biocompatible polymers | Initial structure | Structure | | Substitution degree | | |
|---|---|---|---|---|---|---|---|
| | | | Mol. weight[b] | Z | X = CM x | Y = SO3 y | Z z |
| 3, 5, 6, 12 | RGTAC-27 | Dextran | 40 | Phenylalanine methyl ester | 0.76 | 0.81 | 0.18 |
| 3, 13 | RGTAC 29 | Dextran | 200 | Phenylalanine methyl ester | 0.57 | 0.87 | 0.18 |
| 3, 13 | RGTAC-31 | Dextran | 500 | Phenylalanine methyl ester | 0.46 | 0.88 | 0.27 |
| 3, 6 | RGTAC-32 | Dextran | 2000 | Phenylalanine methyl ester | 0.47 | 0.88 | 0.22 |
| All examples | RGTAE-82 | Dextran | 40 | Acetate | 0.4 | 1.00 | 0.18 |
| 1, 3, 5, 6, 10 | RGTA-21 | Dextran | 40 | Benzylamine | 0.82 | 0.95 | 0.47 |
| 3, 11, 12, 13 | RGTAE-61 | Cellulose | ~90 | — | 0.39 | 1.13 | — |
| 3 | RGTAE-57 | β glucan | Nd | — | 1.04 | 0.89 | — |
| 1, 3 | | Carboxymethyl-cellulose | | | | | |
| 1, 3, 5, 6 | | Glucuronan | 200 | Acetate | 1 | −0.85 | 0.70 |
| 3 | | Glucoglucuronan | 550 | | 0.5 | 0.9 | — |
| 3, 5, 6 | RGTA MP4 | Copolymer of malic acid | 6300 | S-butyl | 0.65 | 0.25 | 0.10 |
| 3, | RGTAFU | Fucane | Nd | | 0.7 | 1.8 | — |
| 3, 5, 6 | RGTALG | Alginate | Nd | | 1 | 0.7 | — |
| 3, 5, 6 | RGTAXA | Xanthane | Nd | | 0.7 | 1.1 | — |
| 3, 5, 6 | Control | Polypensosulphate | 4 to 6000 | | | | | a: example to indicate the number of the example(s) in which the said biocompatible polymer is used.
b: mol. weight. In order to indicate the molecular weight of the initial skeleton serving for synthesis of the biocompatible polymer expressed in kDa.
nd for not determined.

EXAMPLE II

Effects Against Pain of the Biocompatible Polymers

1) Example 1: Superficial Skin Burns:
+Following Exposure to the Sun

First degree burns induced by prolonged exposure to the sun's radiation were treated with compositions containing at least one biocompatible polymer. The burns were located on the face, back, abdomen, arms, legs and/or the feet. For individuals with bilateral exposure, only one of the sides or limbs exposed was treated, retaining the other side as a reference. The persons within the context of this study involve adults or children of either sex and of ages ranging from 5 years to 60 years. The exposure to the sun was indicated by redness and hypersensitivity to pain with, in some cases, incipient blister formation. All the persons had lesions after exposures of variable duration, sometimes one hour only and occasionally several hours, for example, exposure to the sun of the Bahamas between 11 a.m. and 5 p.m. during the first period in April. In all cases, this involved a first exposure after the winter period. In the evening at around 9 p.m., fifteen individuals suffering from moderate or severe, but permanent pain were treated by local application of a solution of biocompatible polymers at 100 micrograms per ml in physiological saline in methylcellulose excipient in order to lend a slight pasty consistency to the solution and facilitate its application and its adhesion to the skin. The volumes used were just sufficient in order to cover the surface of the area to be treated and application consisted of a very light passage of the hollow of the hand in order to spread the pasty solution of biocompatible polymers.

In all cases, the persons noted very pronounced relief within a period of 10 to 30 minutes, or even disappearance of the feeling of pain on the side treated with biocompatible polymer (back, abdomen, face or limb); whereas the contralateral side was still painful and remained very sensitive to the touch. The pain had not reappeared again on the following morning on the regions treated whereas it was still persistent in the untreated burned areas. According to the extent of the burn and depending on the cases after around twenty hours, the pain had reappeared and treatment was subsequently repeated. In these examples, the pain had disappeared after 48 hours in all the cases, since still superficial burns were involved.

Similar observations were recorded with application of biocompatible polymer only in physiological saline, at the same concentrations as described above.

In other similar examples, the biocompatible polymer also had an effect in relieving pain, even if its application was performed on skin previously treated with products containing fats such as Vaseline or Biaffine (Medix). The only constraint in this case involved taking care to spread the aqueous solution of biocompatible polymers well so that it did not run away from the area to the treated during application to the skin. These same effects were observed even if the biocompatible polymer was applied at a later stage after the burn.

The effects of the biocompatible polymer are independent of those of aspirin or paracetamol or other anti-inflammatory or analgesic agents often associated with pain relief as is the case after sunburn. Therefore, the differential analgesic effects of the biocompatible polymer distinguish themselves from and add themselves to those of these agents and when a single burned side is treated with a biocompatible polymer in an individual who has taken (via the oral route) aspirin or paracetamol (up to 1 gram every 6 hours), the burned side treated with biocompatible polymer has achieved more relief than the contralateral. The same experiment was repeated in some ten other individuals and the same result was obtained every time.

+After Laser Treatment:

Effects of relief were observed after applications of biocompatible polymer by vaporisation on to skins treated with a laser in a "resurfacing" protocol. The polymer was in solution in this case in physiological saline at a concentration of 100 micrograms per ml.

2) Example 2: Effect Against Pain of the Biocompatible Polymer on Deep Skin burns.

Several cases of deep burns underwent treatment with a biocompatible polymer and each time, major relief or even disappearance of the sensation of pain was observed in the tens of minutes following the application and lasted a period of several hours.

Therefore, a man of 55 years of age was burned at around 9 p.m. by a product derived from heavy derivatives of petrol and extensively used to start and rouse barbecue fires. The burn was diagnosed by two physicians successively on the very evening and the following morning as being of deep second degree over an area representing mainly approximately half that of the outer side of the hand with the thumb, index and middle finger and a few areas of the palm extending to the wrist.

The pain was extremely acute and the injured man needed, in the opinion of a surgeon who was a specialist in burns and who had witnessed the accident, to be taken to hospital and treated with strong analgesics (Diantalvic or morphine), suggesting the possibility of a skin graft in order to recover full tissular integrity. Approximately two hours after the accident, a solution of biocompatible polymer at 100 microg./ml in physiological saline soaked into sterile gauzes was applied to the burned parts. These gauzes were subsequently covered with tulle gras which itself was impregnated with Vaseline.

During the quarter of an hour following application of the biocompatible polymer, the pain had become completely tolerable and the pain had sufficiently diminished for the burned man to go to sleep without difficulty and wake up with the sensation of almost complete disappearance of the feeling of pain. On the following day, the change of dressing according to the same principle as on the day before further increased the feeling of wellbeing.

The effect of relief and even total elimination of pain persisted throughout the entire duration of the treatment, consisting solely of applying a gauze soaked in the solution of biocompatible polymer to the lesions for around ten days.

3) Example 3: Effect Against Pain of the Biocompatible Polymer Against Deep Second Degree Burns in Rats.

The rat model consists of burns performed on the back of hairless rats. The model was standardised by preliminary studies which established the reproducibility of the study model. Originally, this model aimed to assess the effect of treatment with a biocompatible polymer on the cicatrisation of the burns and more specifically with regard to re-epidemmisation, angiogenesis and remodelling of the dermis. In the study presented below, only the effects of biocompatible polymers as agents against pain were reported, observed by means of the criteria scored from 1 to 5 mentioned above.

a) Presentation of the Model.

The model consists of a burn obtained by application for 4 seconds of a brass cylinder 2 cm in diameter heated to 100° C. in a boiling water bath. The coagulation necrosis caused by application of this cylinder to the skin of the hairless rat is not totally uniform from one point of the burn to another. On histological examination after three days, three areas may be distinguished ranging from the periphery to the centre of the burn, areas on which the gradual thickness of the coagulation necrosis is responsible for burns of increasing depth. These three areas correspond to different degrees of burning.

Therefore, the peripheral area of the burn in which the coagulation necrosis only affects the horny layer of the epidermis corresponds to a first degree burn. The intermediate area of the burn in which the coagulation necrosis extends from the epidermis to the granular layer or to the superficial part of the mucous body of Malpighi. This coagulation necrosis also affects the epithelium of the piliary infundibula over an equivalent thickness. A superficial second degree burn is involved. Finally, the central area of the burn in which the epidermis is necrosed throughout its entire thickness represents 50 to 60% of the total area burned and corresponds to a deep second degree burn.

Therefore, according to the areas, the necrosis spares or does not spare the epidermal basal membrane and affects or does not affect the adjacent part of the papillary dermis. A deep second degree burn or an intermediate superficial burn is involved. Necrotic lesions identical to those of the dermis are observed in the epithelium of the pililary infundibula and extent more or less completely to the contents of the sebaceous glands.

b) Experimental Protocol.

Fourteen mail hairless rats, weighing between 280 and 300 grams, were randomly distributed to two groups of 7 rats. Following anaesthesia of the rats according to the regulatory protocols for animal experimentation, the burns were performed according to the protocol described above.

Five minutes after the burns were performed, the animals in the treated groups (G+) and reference (G−) received a topical application of 1 milliliter of physiological saline containing or not containing 100 micrograms per milliliter of biocompatible polymer, soaked into a sterile swab. A few minutes afterwards, each animal received an intramuscular injection (IM) of physiological saline containing or not containing biocompatible polymer (1.5 milligrams per kilo) in a volume of 300 microliters. The animals in the G+ groups subsequently received a weekly IM injection of the same dose of biocompatible polymer and those of the G+ groups received an injection of physiological saline. The occlusive dressings consisted of a layer of tulle gras, with a film of Jelonet, Opsite (10×14 cm, Smith and Nephew) on top. The whole was covered with sticking plaster covering the entire abdomen of the animal.

The dressings were changed every 2 days during the first week and weekly during the first month. The animals kept in individual cages no longer had any dressing one month after the operation.

c) Measurement of the Animals' Suffering.

On D1, D3, D5 and D7, during the changing of dressings, a difference was observed in the behaviour of the animals treated with biocompatible polymer (+) in relation to the untreated animals (−). The treated animals were much more calm and were handled by the experimenter without struggling and do not cry out. In order to avoid interferences, the changes of dressings were performed in a room apart from the place in which the animals were kept and the individual ages were removed at random (rats treated or untreated with a biocompatible polymer had their dressings changed without any pre-established order). The experimenter, who was not informed of the treatment of the animals with a biocompatible polymer, with a double-blind protocol, scored the following parameters from 1 to 5:

Parameter (a): ease with which the rat allows itself to be handled (1 being the most easy);

Parameter (b): ease with which it allows the dressing to be removed;

Parameter (c): reaction to palpation (touch) of the burned area;

Palpation was performed by application of the brass tube used previously for the burn, but at ambient temperature, applied without pressure to the centre of the wound and maintained in the upright position with the hand for 5 seconds.

Parameter (d): reaction to palpation in the peripheral area of the wound;

Following the palpation experiment, the animal's reaction to skin movements was measured. This was performed by pulling the healthy skin taken between the thumb and index finger of each hand of the experimenter placed on each side at approximately 3 cm from the initial centre of the burn and by 4 slow to and fro movements of a distance of 2 cm according to an axis perpendicular to the vertebral column, the animal being held by a second experimenter by the base of the neck and hind legs.

Parameter (e): ease with which the rat allows itself to be treated for cleaning of the wound with detergent and replacement of the dressing;

Parameter (f): whether the animals emit audible signs of suffering at each of these stages.

Table 3 below summarises the experimental results obtained.

TABLE 3

|  | Days | | | | | | | |
| --- | --- | --- | --- | --- | --- | --- | --- | --- |
|  | D1 | | D2 | | D5 | | D7 | |
| Treatment with RGTA | − | + | − | + | − | + | − | + |
| Parameter a | 5 | 2 | 5 | 1 | 2 | 1 | 2 | 1 |
| Parameter b | 5 | 3 | 3 | 2 | 3 | 1 | 3 | 1 |
| Parameter c | 5 | 3 | 5 | 2 | 5 | 1 | 3 | 1 |
| Parameter d | 5 | 3 | 5 | 2 | 5 | 1 | 4 | 1 |
| Parameter e | 5 | 2 | 4 | 2 | 4 | 1 | 4 | 1 |
| Parameter f | 5 | 2 | 5 | 1 | 3 | 1 | 3 | 1 |

Score of 1 to 5 in ascending order of assessment of the criteria.

Score of 1 to 5 in ascending order of assessment of the criteria.

It should be noted that these effects against pain of the biocompatible polymer are observed well before the effects on cicatrisation which only appear in this model 8 to 10 days after the burn, the time required in order to eliminate the necrotic tissues.

4) Example 4: effect against pain in normal humans suffering from severe skin ulcers of all origins and peripheral neuropathies, particularly in diabetics and alcoholics.

Ten cases of skin ulcers in humans were treated. These involved compassionate cases, all presenting with stage 1V arteritis for which no treatment had had any effect and for which amputation of the limb as inevitable and scheduled as the only alternative to a morbid prognosis.

Two protocols were used:

a) the first consisted in applying to the wound after cleansing with detergent, a sterile gauze (10×10) previously soaked with 5 ml of biocompatible polymer at 100 micrograms per ml in injectable physiological saline in humans and leaving it on the skin for 10 minutes. The gauze was removed and the dressing was performed in the conventional manner. The first 8 cases below were treated according to this protocol.

The first case involved a man of 75 years of age, with an ulcer on the internal malleolus over a very wide area, which had been refractory to all treatment for two years and under morphine (Skenan, 2×90 mg/day). From the first day of treatment onwards, the patient experienced relief of the pain which completely disappeared after 14 days. Evidently, the patient stopped taking his analgesic medication. It should be noted that the effect against pain of the biocompatible polymer appeared well before the effect on cicatrisation, which extended over a period of more than two months.

The second case involved a man of 69 years of age, diabetic and whose dorsal side of the foot was so deeply ulcerated that the tendons were bare. The ulcer had been refractory to any treatment for more than 6 months and this patient was under morphine analgesia. The treatment with the biocompatible polymer allowed such a relief of pain that after 14 days the patient stopped taking his analgesics.

The third case involved a woman of 50 years of age, who had already undergone an amputation and whose stump was ulcerated. The ulceration progressed and complete amputation of the stump up to the hip was scheduled. This woman was under morphine and benzodiazepines. Application of the biocompatible polymer allowed such a relief of pain that after two weeks, the patient stopped taking both the morphine and the benzodiazepines.

The same effects against pain of the biocompatible polymer were observed in the five further cases treated.

b) The second administration protocol of the biocompatible polymer involved oral administration and consisted in giving a solution of 70 ml of polymer in water to drink every morning in the fasting state at concentrations which, according to the patients, ranged from 0.01 to 10 mg/kg (weight of the patient). All the patients treated (3 cases) were relieved of their pain and very markedly so after 15 days of treatment. The effect against pain appeared more rapidly at the high doses, but was obtained in the long term with the lowest doses.

The majority of the cases treated above were diabetics. It was apparent from this study that treatment via the oral route also allowed relief of neuropathies, particularly of the lower limbs in diabetics and/or alcoholics and even in some patients suffering from AIDS, without these persons suffering from ulcerations. The effect of pain relief was observed in all these cases.

5) Example 5: Effect Against Pain of the Biocompatible Polymer on Pain Caused by Cold Sores.

Labial and genital herpes is a frequent infection which manifests itself by the formation of spots on the lips (also known as cold sores) and mucosae. They progress by swelling, rapidly becoming red and resolve by causing superficial fissures. These different stages correspond to phases of development of the virus and result in increasing pain before the lesions burst and afterwards formation of the fissure until resolution.

Local application of biocompatible polymer by simply spreading with the finger over the spot relieves pain and this relief is also experienced during the bursting and fissuring phase.

The effect of the biocompatible polymers on the cicatrisation of this fissure was foreseeable owing to the effects of the biocompatible polymer on cicatrisation of skin lesions already described, but it was not foreseeable that the effect of the biocompatible polymer against pain would be experienced from the formation of the spot, during its growth and at the time of its opening.

6) Example 6: Effect Against Pain of the Biocompatible Polymer on Pain Caused by Chapping on the Fingers.

The formation of chapping is frequent and affects all populations of both sexes and all ages. These chapping lesions cause a dull pain that increases as soon as the fingers are exposed to dryness, moisture and/or cold.

It has been observed essentially in populations of women of an age of between 40 and 80 years of age who suffer from chapping lesions for several months of the year that a single local application of a solution of biocompatible polymer results in relief of pain. These persons all used commercial treatments based on protective grease or a cream of the Neutrogena type.

The relief is perceptible from the first half hour onwards and generally persists, since it is accompanied by rapid closing of the cutaneous microlesions causing the chapping within the subsequent 24 to 48 hours without any need to apply the biocompatible polymer again.

It was therefore possible to treat several tens of individuals with the same success every time. The biocompatible polymer treated the pain in all cases in addition to the discomfort caused by the chapping initially and the skin microfissures secondarily.

A synergic effect of the biocompatible polymer with antibiotic creams (aureomycin or neomycin at 2%) was often observed.

7) Example 7: Effect Against Pain of the Biocompatible Polymer on the Pain and/or Itching Induced by Hyperkeratinisation of the Skin or by Psoriasis or by Eczema and by herpes zoster.

An effect of calming of the skin irritation or the itching caused by dermatitis of various origins was observed in different cases following treatment with biocompatible polymers.

Therefore, a dentist whose hands had become hyperkeratinised following dermatitis refractory to all treatment and suffering to such an extent that he could no longer exercise his profession was relieved by application of biocompatible polymer in a solution or in an ointment (for example, in a gel charged with carboxymethyl cellulose), whereas only corticosteroids in an ointment had allowed him relief but not with the same efficacy and above all, it had not been possible to continue the treatment. Daily treatment of 15 days with the biocompatible polymer followed by one weekly application had been sufficient in providing a lasting solution to this problem.

The same applied to the relief provided by painting fissures which form under the feet in highly keratinised areas. These fissures may be very painful. The application of biocompatible polymer provides pain relief and this effect was observed in several individuals. One of the most striking effects of the biocompatible polymer of the invention involves calming of itching, whether local or general. Therefore, several cases of local or systemic itching of multiple origin were calmed by local application or absorption per os of the polymer of the invention.

8) Example 8: Effect of Relief and Against Pain of the Biocompatible Polymer on Irritation of the Mucosae or the Skin, in Addition to the Effect Against Pain Following a Surgical Operation.

Local application of the biocompatible polymer to the mucosae and/or irritated skin or to closed scars relieves the pain, the itching and the sensation of burning caused by these irritations or without a known cause. This observation was made in a large number of cases, whether the irritation is of mechanical origin (rubbing of the nose with handkerchiefs, of the tongue on the lips, etc. . . . ) and/or whether it is due to a lack of secretion of lubricant by the appropriate glands (lachrymal, salivary, vaginal, etc. . . . ) or caused by other factors such as excess secretion in the case of rhinitis. The relief of pain and itching in closed scars which are often still turgescent was very marked following local application of the polymer in the gel or cream formulations. We were also surprised to see that these scars, as treatment progressed, diminished in thickness and became much finer, with a marked reduction in redness at the same time. These two unexpected effects were studied comparatively in the same individual in large scars or in symmetrical scars. Therefore, on the abdomen, scars running from one side of the umbilicus to the other (following colectomy) or on the sternum (following cardiac surgery), the lanky scar was divided into three equal parts by marks drawn on a cardboard mask covering all the skin around a slit leaving the scar and its edges visible and accessible over a width of approximately 2 cm. The treatment with biocompatible polymer was administered by applying with the finger gel containing either the biocompatible polymer of the invention or the gel alone to either the upper or the lower part of the scar for 15 days. The pain was markedly reduced to the point of having disappeared in certain cases in the part treated with the polymer, whereas it remained marked in the untreated area. Likewise the scar had been extensively reduced in the area treated with the polymer of the invention and its redness had also decreased in comparison to the area treated with the vehicle. A similar and even more marked observation was made in the case of scars located on symmetrical areas such as those derived from bilateral mammaplasty or the two scars behind both ears made during a lifting.

The applicant naturally investigated whether this effect against pain was observed following surgery. It was possible to propose oral administration of the polymer on waking from the anaesthesia and twice daily thereafter, in the morning and evening, of 2 times 25 ml of the solution of the polymer in water at concentration of 10 micrograms to 10 milligrams of one of the biocompatible polymers. The effect against pain was observed following different types of surgery, such as orthopaedic surgery (insertion of a hip replacement, repair of bone faults on tibias, dental implant surgery, abdominal surgery: appendicitis and colectomy).

9) Example 9: Effect Against Pain of the Biocompatible Polymer on Skin Lesions Caused by Radiotherapy.

Treatment of cancers by radiotherapy causes painful burns and skin microlesions in the irradiated area. Several patients were sometimes treated before irradiation, but always afterwards with biocompatible polymer applied in drops, as a spray, or as a gel to the irradiated area. In all cases, the pain was relieved during the hour following irradiation. The application of biocompatible polymer as an ointment before irradiation was also effective in order to reduce pain preventively.

10) Example 10: Effect Against Pain of the Biocompatible Polymer on Ear Drum Pain.

In one adult case (a man of 56 years of age) suffering from painful bilateral otitis on both sides, biocompatible polymer was instilled in drops on one single ear drum. The effect against pain of the biocompatible polymer was only perceived in the treated ear. Since the pain in the treated ear had returned on the following day, the second instillation was performed this time on both ear drums, both of which were relieved.

11) Example 11: Effect Against Pain of the Biocompatible Polymer on Corneal Pain.

The model used is that of induction of ulcers in rabbit corneas by application of a disc 0.5 mm in diameter soaked in NaOH solution. On the day of ulceration, the anaesthetised rabbits were treated by instillation of two drops of biocompatible polymer in a solution at 100 micrograms per ml in physiological sales or by instillation of two drops of physiological saline alone (control).

On the following day, the analgesic effect of the anaesthesia having disappeared, the rabbits showed extremely different sensitivity depending on whether or not they had received treatment with the biocompatible polymer. The treated rabbits allowed their eyes to be opened without any cries and showed no visible photophobia. Instillation of biocompatible polymer is immediately received as a relief, whereas instillation of physiological saline does not appear to provide any relief in the reference population.

These effects observed in rabbits have since then been confirmed in humans. Therefore, an effect of comfort and relief was perceived in individuals wearing contact lenses and who experienced discomfort and irritation indicated by stinging. Instillation of one drop of a solution of biocompatible polymer provided immediate relief and allowed continued wear of these lenses, whereas without biocompatible polymer, the lenses need to be removed. The effect was even more perceptible in individuals treated with laser as part of corrective surgery. The discomfort, which is sometimes painful for a few days and caused by this surgery disappears by simply instilling one to two drops of biocompatible polymer in a solution at 100 micrograms/ml once or twice a day.

12) Example 12: Effect Against Pain of the Biocompatible Polymer on Burns of the upper respiratory tract.

This same relief was observed following pulmonary intoxications and burns, the origins of which were inhalation of smoke from fires or toxic gases. In this case, the biocompatible polymer was inhaled after being prepared as an aerosol.

Therefore, during a fire caused by burning wood, the heavy smoke emitted resulted in respiratory suffocation and painful lung burns. Inhalation of biocompatible polymer sprayed as an aerosol resulted in rapid relief of the pain. The biocompatible polymer was in aqueous solution in physiological saline at 100 micrograms/ml and the aerosol was performed using a glass capillary tube immersed in the solution in addition to a gas pressure system propelling the biocompatible polymer through this capillary. This same effect of pain relief was observed following accidental inhalation of formol vapour.

13) Example 13: Effect Against Pain of the Biocompatible Polymer on Respiratory Tract Pain Related to Asthma and Rhinitis.

Several individuals presenting with respiratory allergy phenomena of different origins (hay fever, allergy to cat or rat hair) were treated with aerosols obtained by spraying biocompatible polymer, the subject of the present invention, directly into the nostrils using a bottle equipped with an atomiser. This treatment administered in the middle of a bout brings rapid relief of pain.

This observation was reproduced several times in the same individuals and brought relief on each occasion. It was observed that the frequency of the bouts decreased as a function of the number of treatments. Likewise, treatment with a biocompatible polymer according to the invention reduces the feeling of suffocation and the coughing bouts caused by exposure to tobacco or other irritants.

In all cases, the concentrations used were between 1 and 100 micrograms per ml, according to the polymer used and placed in solution, being initially, before the formation of an aerosol, in a sterile aqueous solution.

As the pain followed by the discomfort disappeared, so did the other symptoms and surprisingly, by treating the pain the disease was also treated, at least for a period of several months. It should be noted that in some cases, the treatment by inhalation of biopolymers of the invention was conducted in addition to and without modifying the treatments and dosages in progress. Therefore administration of corticosteroid products and beta 2 antagonists does not appear to interfere with the action of the biopolymers.

14) Example 14: Effect Against Pain of the Biocompatible Polymer on Discomfort and Pains Related to Bronchial Obstruction.

The discomfort and pains following obstruction of the respiratory tracts resulting from infections or irritations or obstructions of the bronchi as in cystic fibrosis in the acute or chronic forms were relieved by inhalations of polymers prepared as aerosols but also by daily absorption by the oral route of solutions ranging from 0.01 to 10 mg/kg according to the cases and types of polymers used.

As treatment of the pain and the respiratory discomfort progressed, and improvement in the symptoms of the disease was observed. In some cases, the emphysema appeared to be treated insofar as the pain did not return and respiratory function markedly improved.

15) Example 15: Effects on Calming Cough of the Biocompatible Polymer.

Cigarette smoke is a frequent source of irritation of the throat, nose and bronchi and may result in a regular cough or bouts of coughing. The latter may become genuinely painful. Absorption via the oral route with gargling or by atomisation or by respiration as an aerosol of the biocompatible polymer has an effect of relieving or stopping the discomfort caused by these rapid smokes.

16) Example 16: Effects Against Pain of the Biocompatible Polymer on Ulcerations of the Stomach.

The effects against pain on ulcerations of the stomach were observed in two cases.

The first was an African man of 45 years of age suffering from a stomach ulcer diagnosed by endoscopy but not treated (by antibiotic treatment against Helico Bacter) and sufficiently severe in order for the pain to impose an alcohol-free diet without any gastric excitants (spices, coffee, etc.). In spite of this diet, this man suffered from a permanent burning sensation, particularly exacerbated at mealtimes. Intake by the oral route of 20 ml of biocompatible polymer in solution in physiological saline at 100 micrograms per ml every three days eliminated all pain from the first day of treatment onwards, which lasted three weeks without recurrences after 6 months.

The other case is a man of 57 years of age whose burning sensations in the stomach are regularly calmed within the minutes following intake of a mouthful of 20 ml of biocompatible polymer.

17) Example 17: Effect Against Pain of the Biocompatible Polymer on Diffuse Abdominal Pains.

A man of 55 years of age weighing 70 kg presenting with diffuse abdominal pains with increasing frequency and intensity, subsequently disappearing before reappearing a few days later was effectively calmed on several occasions by an oral administration of 70 ml of the biocompatible polymer which is the subject of the present invention. During the half hour following administration, the pain had disappeared. This man was suffering from nephritic colic and the effect against pain obtained by this oral administration was only effective in the initial phases of the colic. During more intense pains, only morphine was capable of being effective. It is this observation that allowed realisation of a systemic action against pain of the biopolymer via oral administration. A woman of 55 years of age, suffering from inoperable cancer of the pancreas, survived without having to increase a basal level of morphine of 50 mg per day until a very late stage, without the pain becoming intolerable with an oral and daily administration of 100 micrograms/kg of the polymer in solution in water. Not the slightest interference appears to exist with morphine other than an additive effect against pain.

18) Example 18: Effect Against Pain of the Biocompatible Polymer on Headaches.

The effect of the biopolymer on headaches was observed in some ten cases after an oral administration of the product according to the same conditions as in example 15. Here again, it was possible to markedly reduce the headache and sometimes eliminate it totally. In two of the treated cases, the individuals, who were used to severe migraine and who, in general, did not obtain any relief with conventional analgesics (aspirin, paracetamol) were no longer in any pain.

19) Example 19: Effects Against Pain of the Biocompatible Polymer On aphthous Ulcers, Mucitis, Sore Throats and on Dental Pains.

Application of biocompatible polymer, either directly to the buccal aphthous ulcers using a cotton bud soaked in biocompatible polymer or by a simple mouthwash results in a radical reduction in pain.

The same applies to pains in the gums caused by receding gums. In this case, we observed improved efficacy following brushing of the teeth and the sensitive areas impregnated with a brush soaked in a biocompatible polymer solution.

The effect against pain was observed in a series of experiments in a model of periodontitis induced in hamsters. The experimental model is such as that published in Escartin et al., "A new approach to treat tissue destruction in periodontitis with chemically modified dextran polymers", *FASEB J.*, 2003, vol. 17, 636-643. In this series of experiments, the animals treated with an injection via the intramuscular route of biocompatible polymer at 0.4 mg/kg or at 1.5 mg/kg apparently suffered less than those who did not undergo any treatment. The reduction in pain was assessed based on behavioural criteria and on the appearance of the fur and was indicated by less hypersensitivity of the animals to the stresses represented by the approach of an experimenter and agitation in the presence of noise and above all by more rapid intake of the food rations, suggesting less discomfort of the animals treated with a biocompatible polymer.

Likewise, a woman of 52 years of age, suffering from throat pains and voice loss obtained relief by mouthwashes and gargles with a biocompatible polymer.

The pronounced effect on relief of the pains of mucitis induced following chemotherapy and radiotherapy as observed after a mouthwash with the polymer of the invention. Several individuals suffering from grade 2 and 3 mucitis obtained relief after mouthwashes from the pains that are very difficult to bear resulting from the formation of ulcers in the mouth and throat. A patient suffering from Behçet's disease also obtained great relief by a mouthwash in the morning and evening during the few days that the painful bout lasted. The polymer was simply in an aqueous solution at 100 micrograms per ml.

20) Example 20: Effects Against Pain of the Biocompatible Polymer on Tendons

Several cases of tendon pains were treated with a biocompatible polymer administered by simple massage to the painful site. In this manner, the following observations were made.

An adult of 57 years of age, left-handed and a tennis player had painful tendonitis of the left elbow and had ceased playing this sport after having undergone several treatments including several local corticosteroid injections at 6-month intervals and total cessation of tennis for two year. The pain had disappeared, but reappeared at the slightest effort involving his elbow tendons. Following a day that had placed a major burden on his elbow, this man had intense elbow pain. The local application of biocompatible polymer by massage with a solution at 100 micrograms per ml in physiological saline allowed complete disappearance of this pain within a few tens of minutes.

Likewise, it was observed that local injection or application as an ointment of biocompatible polymers on the painful areas of the tendons such as for the elbow or the knee rapidly and durably relieves the pain. Therefore, in several types of tendonitis of the elbow, such as "tennis elbow" or ischaemic tendons of the knee as in Osgood-Schlatter's disease or in pains in the tendons of the feet such as the Achilles tendon in athletes, administration of biocompatible polymer results in effects of rapid and major relief of pain.

The same treatment was applied to racehorses suffering from tendonitis of the joint areas of the legs. Therefore, a series of injections in the peritendinous area of a few tens of microliters of biocompatible polymer allowed relief of pain and this relief was indicated by an absence of claudication after about a fortnight. The treatment was continued with a weekly frequency and resumption of training after two months showed absence of claudication, pain on palpation and an improvement in the animals' performance.

21) Example 21: Effects Against Pain of the Biocompatible Polymer on Arthroses or Arthritis.

Several cases of pain resulting from arthrotic or inflammatory problems in the knee joint were relieved by application of biocompatible polymer either in a solution in physiological saline at 100 micrograms per ml or at the same concentrations in an ointment prepared with sodium carboxymethyl cellulose (Aqualon) at 4.5% complement at 100% or a neutral hydroxypropylmethyl cellulose gel (Kucel of aqualon type 99MF EP at 3% complement at 100%). The persons treated were under analgesics (3 tablets of Voltaren SR at 100 per day). A simple massage with biocompatible polymer resulted in relief after a quarter of an hour for a duration of two to three hours. This repeated treatment avoided these individuals Voltaren administrations. After three days of treatment, the pains were experience less and less frequently in spite of normal use of the knee. Finally after approximately a fortnight, application of biocompatible polymer once a day was sufficient in order to avoid any pain.

Similar effects were obtained in the long term when the biocompatible polymer was administered as a drinkable solution. The doses of 0.1 mg/kg to 10 mg/kg are taken in a volume of water of 50 to 100 ml every day (preferably in the morning in the fasting state). Relief was observed in persons suffering from knee pains for several years, thereby preventing practice of sports and rendering walking difficult and painful. After two months of treatment, these individuals no longer experienced this discomfort and/or pain and were able to play their sport again. They did not observe any adverse effects of this treatment over this period.

22) Example 22: Effects Against Pain of the Biocompatible Polymer Following Orthopaedic surgery.

The effect against pain of the biocompatible polymer was observed in a woman of 50 years of age who had just undergone surgery to stiffen the bones of the foot. This involved correction of Hallux Valgus and two other toes by insertion of a metal rod in the bones in order to maintain the axis of the toe in the correct position. This operation already performed in this person three years beforehand had caused very severe pain for more than a week and still severe pain for three weeks. Following the second operation, this person received an intramuscular injection of biocompatible polymer on the basis of 1.5 mg/kg on postoperative days 2, 4 and 8. The pain disappeared during the hours following the first injection and returned on the $2^{nd}$ day and disappeared again within the hour following the second injection of biocompatible polymer on the $4^{th}$ day, only returning on the $7^{th}$ day. It disappeared again in the hour following the repeat injection on the $8^{th}$ day, this time for good.

23) Example 23: Effect Against Pain of the Biocompatible Polymers Against Degenerative Neuropathies.

Two patients who had been suffering from multiple sclerosis for more than 20 years regularly suffered from joint pains and abdominal pains with periodic painful spasms. They both had a fairly similar stage of illness with loss of the use of one leg.

Daily oral administration of approximately 30 ml of an aqueous solution of the polymer of the invention partially calmed their pains and particularly the pain in the hand for one and the joint and abdominal pain for the other. The most surprising fact was to observe, after two months of oral administration of the polymer of the invention in an aqueous solution of 3 to 30 mg per day, a return to slight recovery of the motricity of the paralysed leg. Lifting the heel, followed by the leg and subsequently the ability to move it from back to front without touching the ground and subsequently to lift it sufficiency in order to be able to touch the knees were the objective signs of this recovery. Likewise, the suffering or neuropathies in the legs and hands in type 2 diabetics were markedly relieved after a few weeks of oral administration of the aqueous solution of biocompatible polymers of the invention.

24) Example 24: Effect Against Pain of the Biocompatible Polymer on Cystitis.

The persistent pain of cystitis refractory to antibiotic treatment was relieved in two young women by a daily oral administration of the polymer of the invention, in addition to antibiotic treatment.

The invention claimed is:

1. A method of treating pain associated with a tissue, the method comprising contacting the tissue with a pharmaceutical, dermatological or cosmetic composition or a medical device comprising a biocompatible polymer corresponding to formula (I):

$$A_a X_x Y_y \qquad (I),$$

in which:
A comprises a monomer that is glucose,
X represents a RCOOR' group,
Y represents an O or N-sulphonate group bound to A,
R represents a hydrocarbon chain, possibly branched and/or unsaturated and which may contain one or more aromatic rings and R' represents one hydrogen atom or one cation,
a represents the number of monomers,
x represents the rate of substitution of the A monomers by the X groups, and x is between approximately 20 and 150%.
y represents the rate of substitution of the A monomers by Y groups, and y is between approximately 30 and 150%;
wherein the biocompatible polymer is in an amount effective to provide within minutes of administration, relief of pain, and wherein the method does not treat the condition that causes the pain.

2. The method of claim 1, wherein the mass of the polymers of formula (I) is greater than 2000 daltons.

3. The method of claim 1, wherein the radical R is a linear or branched alkyl, allyl or aryl group.

4. The method of claim 1, wherein the biocompatible polymer comprises functional chemical groups Z, different from X and Y and capable of bestowing additional biological or physical and chemical properties on said polymers, wherein said Z groups are identical or different and are amino acids, fatty acids, fatty alcohols, ceramides or derivatives thereof, or nucleotide sequences.

5. The method of claim 4, wherein the rate of substitution of all the A monomers by Z groups represented by "z" is between 0 and 50%.

6. The method of claim 4, wherein the Z group is a substance capable of bestowing on the said polymers improved solubility or lipophilia.

7. The method of claim 4, wherein the Z groups are identical or different and are therapeutic agents.

8. The method of claim 1, wherein the pain is induced by lesions or irritations in an individual in an area in contact with an outside medium.

9. The method of claim 8, wherein the lesions or irritations are selected among skin lesions, corneal lesions, lesions of the eardrum, lesions of the digestive tract, lesions of the respiratory tract such as lesions of the tissues of the airways and lungs and lesions of the urogenital tract.

10. The method of claim 1, wherein the pain is in the tendons and/or cartilages and/or the joints and/or the back and/or the muscles and in general, following impact and/or diffuse pains in the abdomen or in the head.

11. The method of claim 1, comprising contacting the skin with a cosmetic composition for treatment of pain associated with the skin, cornea or mucosae.

12. The method of claim 1, wherein
the pain is induced by
deep skin burns;
scars and cicatricial tissue;
ulcers of the skin and/or the mucosae and/or the cornea;
peripheral and/or degenerative neuropathies;
cold sores;
chapping;
hyperkeratinisation of the skin, psoriasis, eczema or herpes zoster;
a surgical operation;
radiotherapy;
a lesion of the eardrum;
asthma and/or rhinitis and/or bronchial obstruction;
aphthous ulcers and/or sore throats and/or dental pains; or
arthrosis or arthritis.

* * * * *